US00PP24065P2

(12) United States Plant Patent
Dummen

(10) Patent No.: US PP24,065 P2
(45) Date of Patent: Dec. 3, 2013

(54) ***PHLOX* PLANT NAMED 'DUEPHLOSTRA'**

(50) Latin Name: *Phlox drummondii*
Varietal Denomination: Duephlostra

(71) Applicant: Tobias Dummen, Rheinberg (DE)

(72) Inventor: Tobias Dummen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 13/815,060

(22) Filed: Jan. 28, 2013

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Phlox* plant named 'Duephlostra', characterized by its compact, upright to outwardly spreading and mounding plant habit; freely branching habit; freely flowering habit; and relatively large red-colored flowers.

1 Drawing Sheet

Botanical designation: *Phlox drummondii.*
Cultivar denomination: 'DUEPHLOSTRA'.

BACKGROUND OF THE INVENTION

The present invention relates to a new and distinct cultivar of *Phlox* plant, botanically known as *Phlox drummondii* and hereinafter referred to by the name 'Duephlostra'.

The new *Phlox* plant is a product of a planned breeding program conducted by the Inventor in Rheinberg, Germany. The objective of the breeding program is to create new compact *Phlox* plants with numerous attractive flowers.

The new *Phlox* plant originated from a cross-pollination conducted by the Inventor in Rheinberg, Germany in July, 2009 of *Phlox drummondii* 'Wespohopi', disclosed in U.S. Plant Pat. No. 19,742, as the female, or seed, parent with a proprietary selection of *Phlox drummondii* identified as code number PH06-0499-002, not patented, as the male, or pollen, parent. The new *Phlox* plant was discovered and selected by the Inventor as a single flowering plant within the progeny of the stated cross-pollination in a controlled greenhouse environment in Rheinberg, Germany in May, 2011.

Asexual reproduction of the new *Phlox* plant by cuttings in a controlled environment in Rheinberg, Germany since July, 2011 has shown that the unique features of this new *Phlox* plant are stable and reproduced true to type in successive generations.

SUMMARY OF THE INVENTION

Plants of the new *Phlox* plant have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Duephlostra'. These characteristics in combination distinguish 'Duephlostra' as a new and distinct *Phlox* plant:

1. Compact, upright to outwardly spreading and mounding plant habit.
2. Freely branching habit.
3. Freely flowering habit.
4. Relatively large red-colored flowers.

Plants of the new *Phlox* can be compared to plants of the female parent, 'Wespohopi'. Plants of the new *Phlox* differ primarily from plants of 'Wespohopi' in flower color as plants of 'Wespohopi' have red purple-colored flowers. In addition, plants of the new *Phlox* are more compact than plants of 'Wespohopi'.

Plants of the new *Phlox* can be compared to plants of the male parent selection. Plants of the new *Phlox* differ primarily from plants of the male parent selection in flower color as plants of the male parent selection have white-colored flowers.

Plants of the new *Phlox* can be compared to plants of the *Phlox* 'Wespore', disclosed in U.S. Plant Pat. No. 19,743. In side-by-side comparisons, plants of the new *Phlox* and 'Wespore' differed in the following characteristics:

1. Plants of the new *Phlox* were more compact than plants of 'Wespore'.
2. Plants of the new *Phlox* had larger leaves than plants of 'Wespore'.
3. Plants of the new *Phlox* and 'Wespore' differed in flower color as plants of 'Wespore' had dark red-colored flowers.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of a typical flowering plant of 'Duephlostra'.

DETAILED BOTANICAL DESCRIPTION

The aforementioned photograph and following observations, measurements and values describe plants grown during the summer in 10.5-cm containers in a glass-covered greenhouse in Rheinberg, Germany and under cultural practices typical of commercial production. During the production of the plants, day and night temperatures averaged 18° C. and light levels averaged 4,500 lux. Plants were pinched one time three weeks after planting and were 13 weeks old when the photograph and description were taken. In the following description, color references are made to The Royal Horticultural Society Colour Chart, 1995 Edition, except where general terms of ordinary dictionary significance are used.

Botanical classification: *Phlox drummondii* 'Duephlostra'.

Parentage:

*Female, or seed, parent.*—*Phlox drummondii* 'Wespohopi', disclosed in U.S. Plant Pat. No. 19,742.

*Male, or pollen, parent.*—Proprietary selection of *Phlox drummondii* identified as code number PH06-0499-002, not patented.

Propagation:

*Type.*—By cuttings.

*Time to initiate roots, summer.*—About five days at temperatures about 20° C.

*Time to initiate roots, winter.*—About seven days at temperatures about 20° C.

*Time to produce a rooted plant, summer.*—About three weeks at temperatures about 20° C.

*Time to produce a rooted plant, winter.*—About four weeks at temperatures about 20° C.

*Root description.*—Fine, fibrous; white in color.

*Rooting habit.*—Freely branching; dense.

Plant description:

*Plant and growth habit.*—Compact, upright to outwardly spreading and mounding plant habit; broad inverted triangle; low to moderately vigorous growth habit; freely branching habit with about five main laterals developing per plant with numerous secondary laterals; relatively short internodes; dense and bushy plant habit.

*Plant height.*—About 25 cm.

*Plant width (spread).*—About 25 cm.

*Lateral branches.*—Length: About 20 cm. Diameter: About 3 mm. Internode length: About 3 cm. Strength: Strong. Texture: Pubescent. Color: Close to 145B.

Foliage description:

*Arrangement.*—Opposite, simple.

*Length.*—About 4.8 cm.

*Width.*—About 2 cm.

*Shape.*—Elliptic.

*Apex.*—Apiculate.

*Base.*—Truncate to obtuse.

*Margin.*—Finely serrate.

*Texture, upper and lower surfaces.*—Smooth, glabrous.

*Venation pattern.*—Pinnate.

*Color.*—Developing leaves, upper and lower surfaces: Close to 146A. Fully expanded leaves, upper surface: Close to 146A; venation, close to 146B. Fully expanded leaves, lower surface: Close to 146B; venation, close to 146C.

*Petioles.*—Length: About 1 mm. Diameter: About 1 mm. Texture, upper and lower surfaces: Smooth, glabrous. Color, upper and lower surfaces: Close to 144C.

Flower description:

*Flower type and flowering habit.*—Single rotate salverform flowers arranged in small panicles; flowers face mostly upright to outwardly; freely flowering habit with about four flowers per inflorescence and about 120 flowers developing per plant.

*Fragrance.*—Moderately fragrant; sweet, pleasant.

*Natural flowering season.*—Continuously flowering from summer to late summer in Germany; plants begin flowering about six weeks after planting.

*Postproduction longevity.*—Flowers last about three to four days on the plant; flowers not persistent.

*Flower buds.*—Height: About 8 mm. Diameter: About 3 mm. Shape: Narrowly obovate. Color: Close to 61A.

*Inflorescence height.*—About 2.5 cm.

*Inflorescence diameter.*—About 5.7 cm.

*Flower diameter.*—About 2.3 cm.

*Flower depth.*—About 1.3 cm.

*Flower throat diameter.*—About 3 mm.

*Flower tube length.*—About 1 cm.

*Flower tube diameter, at the base.*—About 1 mm.

*Petals.*—Quantity per flower and arrangement: Five petals in a single whorl and fused at the base into a narrow tube. Length from throat: About 1.4 cm. Width: About 1.2 cm. Shape: Spatulate. Apex: Rounded. Margin: Entire. Texture, petal lobes, upper and lower surfaces: Smooth, glabrous. Texture, throat and tube: Smooth, glabrous. Color: Developing petals, upper surface: Close to 57A. Developing petals, lower surface: Close to 62C. Fully expanded petals, upper surface: Close to 57B; venation, close to 57A; color becoming closer to 59B with development. Fully expanded petals, lower surface: Close to 62B; venation, close to 62B. Flower throat: Close to 64B; venation, close to 64B. Flower tube: Close to 62B; venation, close to 64D.

*Sepals.*—Quantity per flower and arrangement: Five sepals in a single whorl and fused towards the base into a slender tube. Length: About 8 mm. Width: About 1 mm. Shape: Lanceolate. Apex: Narrowly apiculate. Margin: Entire. Texture, upper and lower surfaces: Smooth, glabrous. Color, upper and lower surfaces: Close to 146B.

*Peduncles.*—Length: About 2.5 cm. Diameter: About 1.2 mm. Angle: Upright. Strength: Strong. Texture: Smooth, glabrous. Color: Close to 145B.

*Pedicels.*—Length: About 1.7 cm. Diameter: About 1 mm. Angle: About 30° from peduncle axis. Strength: Strong. Texture: Smooth, glabrous. Color: Close to 145B.

*Reproductive organs.*—Stamens: Quantity per flower: Typically five. Filament length: About 5 mm. Filament color: Close to 157B. Anther shape: Oblong. Anther length: About 2 mm. Anther color: Close to 14A. Pollen amount: Abundant. Pollen color: Close to 14A. Pistils: Quantity per flower: One. Pistil length: About 4 mm. Stigma shape: Bi-parted. Stigma color: Close to 3C. Style length: About 2 mm. Style color: Close to 149C. Ovary color: Close to 144A.

*Seeds and fruits.*—Seed and fruit development have not been observed on plants of the new *Phlox*.

Disease & pest resistance: Plants of the new *Phlox* have not been noted to be resistant to pathogens and pests common to *Phlox* plants.

Temperature tolerance: Plants of the new *Phlox* have been observed to tolerate temperatures ranging from about 5° C. to about 40° C.

It is claimed:

1. A new and distinct *Phlox* plant named 'Duephlostra' as illustrated and described.

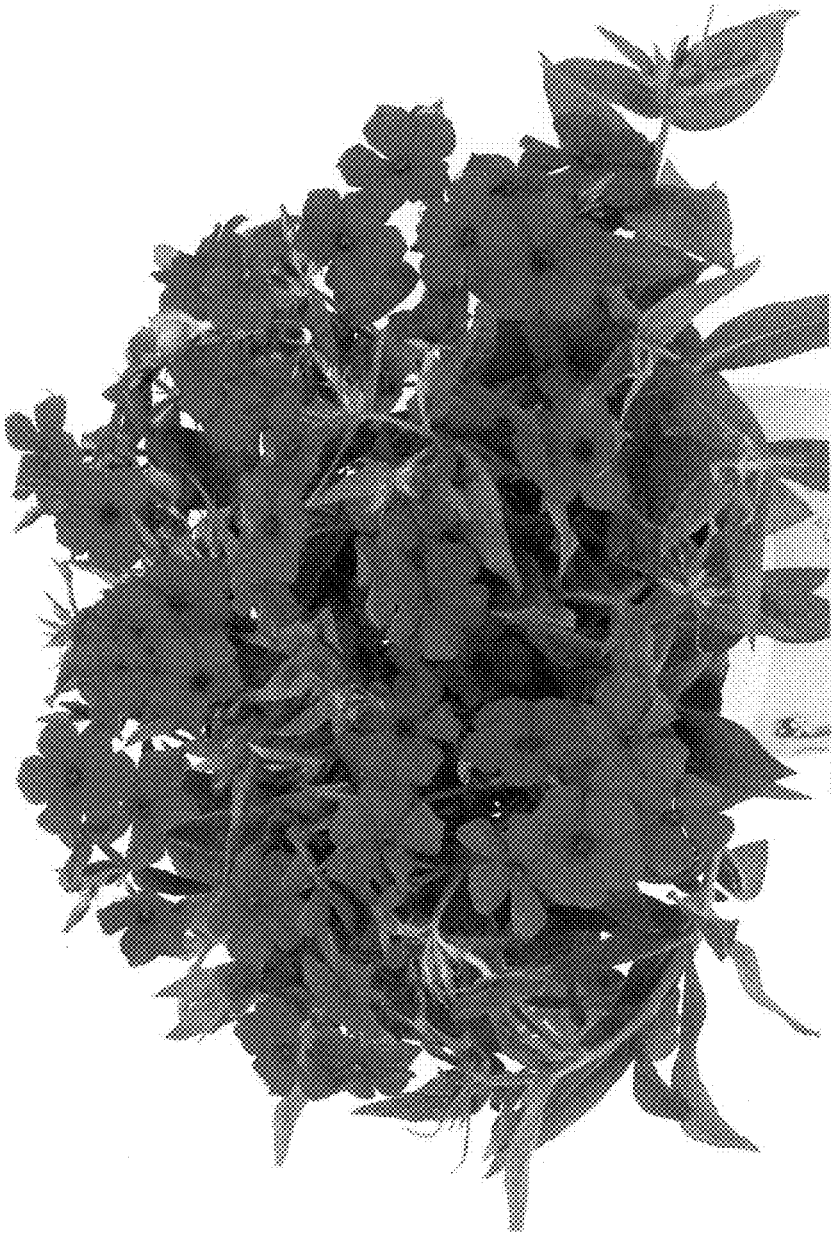

* * * * *